United States Patent
Hasegawa et al.

(10) Patent No.: US 6,774,258 B2
(45) Date of Patent: Aug. 10, 2004

(54) TERTIARY ALCOHOL COMPOUNDS HAVING ALICYCLIC STRUCTURE

(75) Inventors: Koji Hasegawa, Nakakubiki-gun (JP); Takeru Watanabe, Nakakubiki-gun (JP); Takeshi Kinsho, Nakakubiki-gun (JP)

(73) Assignee: Shin-Etsu Chemical Co., Ltd., Tokyo (JP)

( * ) Notice: Subject to any disclaimer, the term of this patent is extended or adjusted under 35 U.S.C. 154(b) by 0 days.

(21) Appl. No.: 10/012,419

(22) Filed: Dec. 12, 2001

(65) Prior Publication Data

US 2002/0072579 A1 Jun. 13, 2002

(30) Foreign Application Priority Data

Dec. 13, 2000 (JP) ......................................... 2000-378693

(51) Int. Cl.[7] .............................................. C07C 69/74
(52) U.S. Cl. ........................ 560/116; 560/117; 560/120
(58) Field of Search ................................ 560/117, 120, 560/116

(56) References Cited

U.S. PATENT DOCUMENTS

| | | | |
|---|---|---|---|
| 3,715,330 A | * | 2/1973 | Nogami |
| 4,440,850 A | * | 4/1984 | Paul |
| 6,150,069 A | * | 11/2000 | Jung |
| 6,159,655 A | * | 12/2000 | Sato |
| 6,225,020 B1 | * | 5/2001 | Jung |
| 6,291,131 B1 | * | 9/2001 | Jung |
| 6,312,865 B1 | * | 11/2001 | Jung |
| 6,348,296 B1 | * | 2/2002 | Jung |
| 6,368,770 B1 | * | 4/2002 | Jung |
| 2001/0051315 A1 | * | 12/2001 | Nishi |
| 2001/0051316 A1 | * | 12/2001 | Nishi |
| 2002/0007031 A1 | * | 1/2002 | Nishi |

FOREIGN PATENT DOCUMENTS

| | | | |
|---|---|---|---|
| JP | 2000-235263 | * | 8/2000 |
| JP | 2000-292917 | * | 10/2000 |
| JP | 2001-89539 | * | 4/2001 |

* cited by examiner

Primary Examiner—Michael L. Shippen
(74) Attorney, Agent, or Firm—Millen, White, Zelano & Branigan, P.C.

(57) ABSTRACT

Tertiary alcohol compounds of formula (1) are novel wherein $R^1$ and $R^2$ are C1–10 alkyl groups which may have halogen substituents, or $R^1$ and $R^2$ may form an aliphatic hydrocarbon ring, Y and Z are a single bond or a divalent C1–10 organic group, and k=0 or 1. Using the tertiary alcohol compounds as a monomer, polymers are obtained. A resist composition comprising the polymer as a base resin is sensitive to high-energy radiation and has excellent sensitivity, resolution, etching resistance and substrate adhesion.

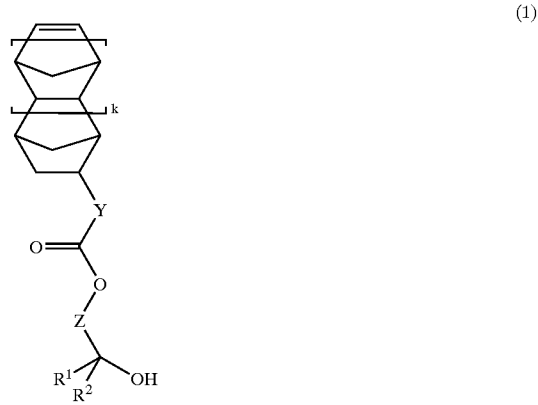

(1)

8 Claims, No Drawings

TERTIARY ALCOHOL COMPOUNDS HAVING ALICYCLIC STRUCTURE

This invention relates to a novel tertiary alcohol compound useful as a monomer to form a polymer which serves as a base resin in chemically amplified resist compositions for microfabrication.

BACKGROUND OF THE INVENTION

While a number of recent efforts are being made to achieve a finer pattern rule in the drive for higher integration and operating speeds in LSI devices, deep-ultraviolet lithography is thought to hold particular promise as the next generation in microfabrication technology. In particular, photolithography using a KrF or ArF excimer laser as the light source is strongly desired to reach the practical level as the micropatterning technique capable of achieving a feature size of 0.3 μm or less.

The resist materials for use in photolithography using light of an excimer laser, especially ArF excimer laser having a wavelength of 193 nm, are, of course, required to have a high transmittance to light of that wavelength. In addition, they are required to have an etching resistance sufficient to allow for film thickness reduction, a high sensitivity sufficient to eliminate any extra burden on the expensive optical material, and especially, a high resolution sufficient to form a precise micropattern. To meet these requirements, it is crucial to develop a base resin having a high transparency, rigidity and reactivity. None of the currently available polymers satisfy all of these requirements. Practically acceptable resist materials are not yet available.

Known high transparency resins include copolymers of acrylic or methacrylic acid derivatives and polymers containing in the backbone an alicyclic compound derived from a norbornene derivative. All these resins are unsatisfactory. For example, copolymers of acrylic or methacrylic acid derivatives are relatively easy to increase reactivity in that highly reactive monomers can be introduced and acid labile units can be increased as desired, but difficult to increase rigidity because of their backbone structure. On the other hand, the polymers containing an alicyclic compound in the backbone have rigidity within the acceptable range, but are less reactive with acid than poly(meth)acrylate because of their backbone structure, and difficult to increase reactivity because of the low freedom of polymerization. Additionally, since the backbone is highly hydrophobic, these polymers are less adherent when applied to substrates. Therefore, some resist compositions which are formulated using these polymers as the base resin fail to withstand etching although they have satisfactory sensitivity and resolution. Some other resist compositions are highly resistant to etching, but have low sensitivity and low resolution below the practically acceptable level.

SUMMARY OF THE INVENTION

An object of the invention is to provide a novel tertiary alcohol compound useful as a monomer to form a polymer for use in the formulation of a photoresist composition which exhibits a high transparency and substrate affinity when processed by photolithography using light with a wavelength of less than 300 nm, especially ArF excimer laser light as the light source.

The inventor has found that a tertiary alcohol compound of formula (1) can be prepared in high yields by a simple method to be described later, that a polymer obtained from this alcohol compound has high transparency at the exposure wavelength of an excimer laser, and that a resist composition comprising the polymer as a base resin is improved in resolution and substrate adhesion.

The invention provides a tertiary alcohol compound having the following general formula (1).

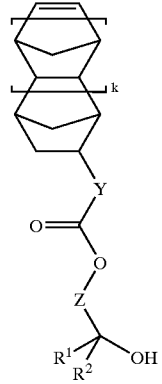

(1)

Herein $R^1$ and $R^2$ are independently a straight, branched or cyclic alkyl group of 1 to 10 carbon atoms in which some or all of the hydrogen atoms on constituent carbon atoms may be substituted with halogen atoms, or $R^1$ and $R^2$, taken together, may form an aliphatic hydrocarbon ring, Y and Z are independently a single bond or a straight, branched or cyclic divalent organic group of 1 to 10 carbon atoms, and k is 0 or 1.

The preferred tertiary alcohol compounds have the following general formula (2).

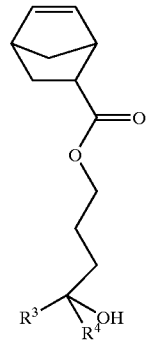

(2)

Herein $R^3$ and $R^4$ are independently a straight, branched or cyclic alkyl group of 1 to 6 carbon atoms.

DESCRIPTION OF THE PREFERRED EMBODIMENT

The tertiary alcohol compounds of the invention are of the following general formula (1).

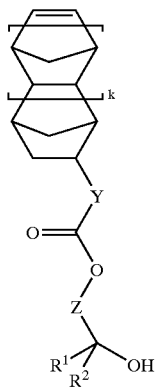

(1)

Herein $R^1$ and $R^2$ are independently straight, branched or cyclic alkyl groups of 1 to 10 carbon atoms in which some or all of the hydrogen atoms on constituent carbon atoms may be substituted with halogen atoms. Examples include methyl, ethyl, n-propyl, isopropyl, n-butyl, sec-butyl, tert-butyl, tert-amyl, n-pentyl, n-hexyl, cyclopentyl, cyclohexyl, bicyclo[2.2.1]heptyl, bicyclo[2.2.2]octyl, bicyclo[3.3.1]-nonyl, bicyclo[4.4.0]decanyl, adamantyl, trifluoromethyl, 2,2,2-trifluoroethyl, 2,2,2,-trichloroethyl, 3,3,3-trifluoropropyl, and 3,3,3-trichloropropyl. Also, $R^1$ and $R^2$, taken together, may form an aliphatic hydrocarbon ring, such as cyclobutane, cyclopentane, cyclohexane, bicyclo[2.2.1]-heptane, bicyclo[2.2.2]octane, bicyclo[3.3.1]nonane, bicyclo[4.4.0]decane and adamantane.

Y and Z are independently single bonds or straight, branched or cyclic divalent organic groups of 1 to 10 carbon atoms. Examples include methylene, ethylene, propane-1,1-diyl, propane-1,2-diyl, propane-1,3-diyl, butane-1,1-diyl, butane-1,2-diyl, butane-1,3-diyl, butane-1,4-diyl, pentane-1,1-diyl, pentane-1,2-diyl, pentane-1,3-diyl, pentane-1,4-diyl, pentane-1,5-diyl, hexane-1,1-diyl, hexane-1,2-diyl, hexane-1,3-diyl, hexane-1,4-diyl, hexane-1,5-diyl, hexane-1,6-diyl, cyclopropane-1,1-diyl, cyclopropane-1,2-diyl, cyclobutane-,11-diyl, cyclobutane-1,2-diyl, cyclobutane-1,3-diyl, cyclopentane-,11-diyl, cyclopentane-1,2-diyl, cyclopentane-1,3-diyl, cyclohexane-,11-diyl, cyclohexane-1,2-diyl, cyclohexane-1,3-diyl, and cyclohexane-1,4-diyl.

The subscript k is equal to 0 or 1.

Of the tertiary alcohol compounds of formula (1), preferred are tertiary alcohol compounds having the following general formula (2).

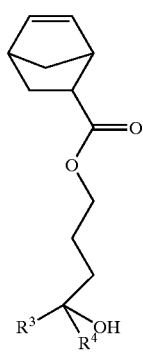

(2)

Herein $R^3$ and $R^4$ are independently straight, branched or cyclic alkyl groups of 1 to 6 carbon atoms. Examples include methyl, ethyl, n-propyl, isopropyl, n-butyl, sec-butyl, tert-butyl, tert-amyl, n-pentyl, n-hexyl, cyclopentyl and cyclohexyl.

Illustrative, non-limiting, examples of the tertiary alcohol compounds of formulae (1) and (2) are given below.

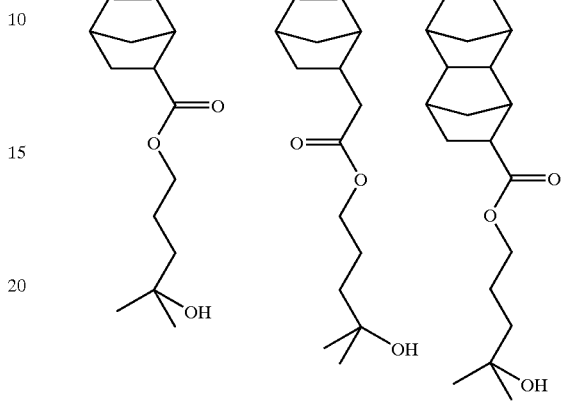

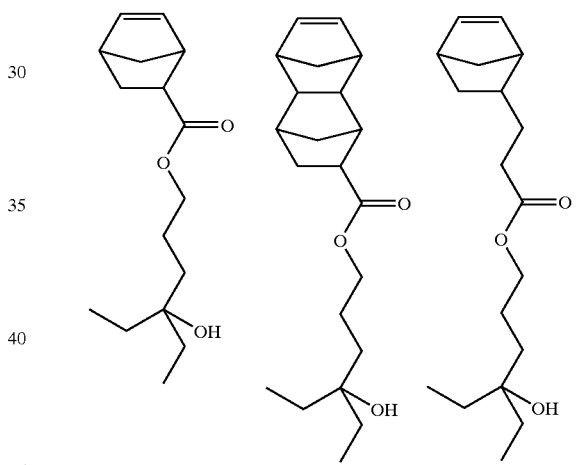

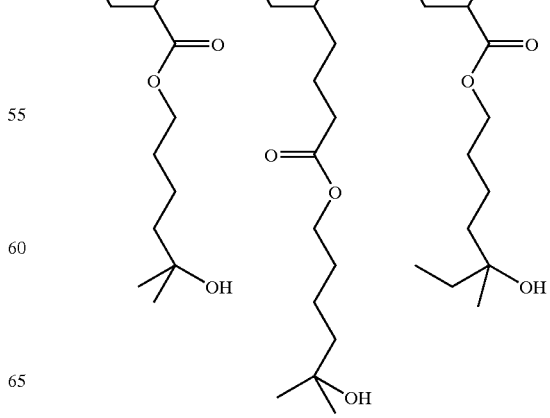

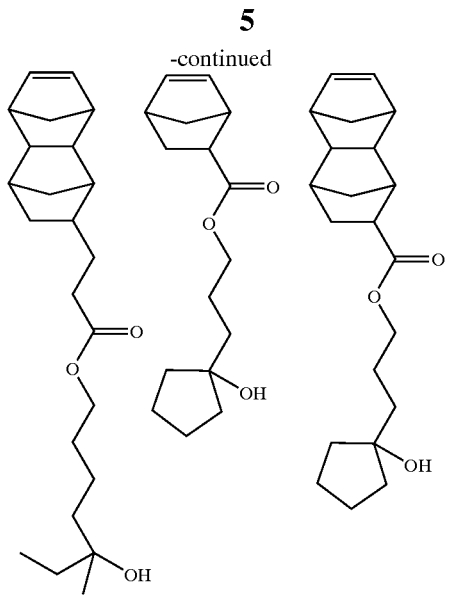

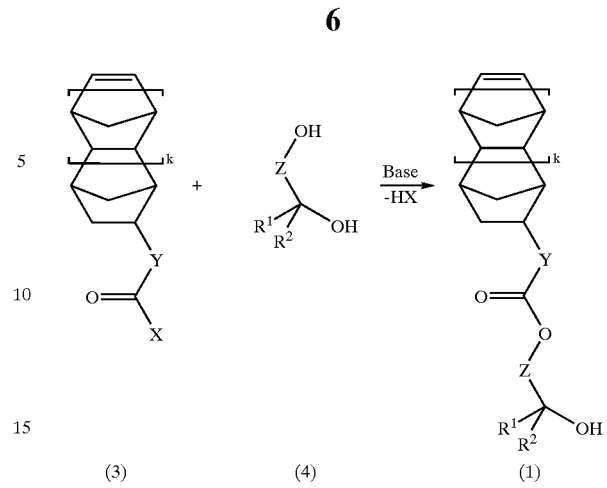

In the above scheme, $R^1$, $R^2$, Y, Z and k are as defined above, and X is a halogen atom.

The base used herein is preferably selected from tertiary amines such as triethylamine, diethylisopropylamine, pyridine, N,N-dimethylaniline, and 4-dimethylaminopyridine, alone or in admixture of any. The amount of the acid halide (3) used is desirably 0.5 to 2.0 mol, and more desirably 0.9 to 1.2 mol per mol of the diol compound (4). The amount of the base used is desirably 1.0 to 20 mol, and more desirably 1.0 to 2.0 mol per mol of the acid halide (3). A solvent may be used although the base itself can serve as the solvent. Suitable solvents are ethers such as tetrahydrofuran, diethyl ether, di-n-butyl ether and 1,4-dioxane, hydrocarbons such as n-hexane, n-heptane, benzene, toluene, xylene and cumene, and chlorinated solvents such as methylene chloride, chloroform and dichloroethylene. The reaction temperature is usually about −50° C. to 80° C., and preferably about 0° C. to 50° C. From the yield standpoint, the reaction is desirably continued to completion while monitoring the reaction by gas chromatography (GC) or silica gel thin layer chromatography (TLC), although the reaction time is usually about 0.5 to about 20 hours. From the reaction mixture, the end tertiary alcohol compound (1) is obtained by a conventional aqueous work-up step. If necessary, the end compound is purified by any conventional technique such as distillation or chromatography.

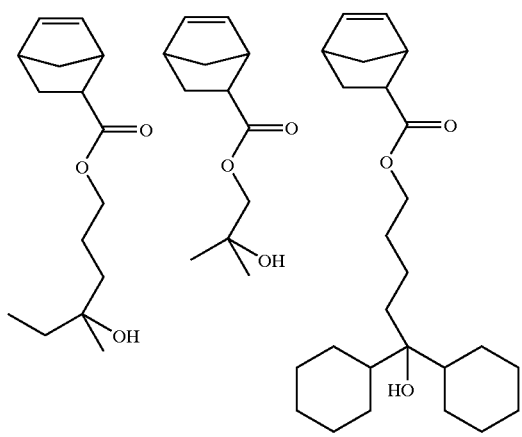

It is believed that when a resist polymer is prepared using the tertiary alcohol compound as a monomer, the tertiary alcoholic hydroxyl groups which are regarded as polar groups for the polymer to become adherent are located at a position spaced apart from the polymer backbone by linkers represented by —Y— and —Z— in formula (1), so that the polymer becomes fully adherent to substrates. It is also believed that when the compound of formula (1) is used as a monomer to form a polymer, the overall polymer can be adjusted in oil solubility and hence, controlled in dissolution properties by selecting $R^1$, $R^2$, Y and Z having an appropriate number of carbon atoms as well as the value of k.

The tertiary alcohol compounds of formula (1) can be prepared by the following two methods, for example, although the method is not limited thereto.

The first method is to synthesize a tertiary alcohol compound (1) through esterification of a diol compound (4) using an acid halide (3) and a base.

The second method is to synthesize a tertiary alcohol compound (1) through transesterification of a diol compound (4) with an ester compound (5) in the presence of a catalyst.

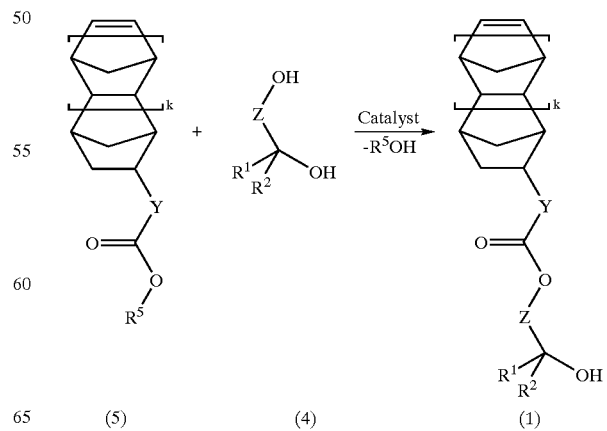

In the above scheme, $R^1$, $R^2$, Y, Z and k are as defined above, and $R^5$ is an alkyl such as methyl or ethyl.

The reaction can proceed in a solventless system although a solvent may be used in a supplemental manner. Exemplary solvents include ethers such as tetrahydrofuran, diethyl ether, di-n-butyl ether, and 1,4-dioxane, and hydrocarbons such as n-hexane, n-heptane, benzene, toluene, xylene and cumene, alone or in admixture of any. Examples of the catalyst used herein include metal alkoxides such as sodium methoxide, sodium ethoxide, potassium t-butoxide, magnesium ethoxide, titanium(IV) methoxide, titanium(IV) ethoxide, and titanium(IV) isopropoxide; organic amines such as triethyl amine, N,N-dimethylaminopyridine, and 1,8-diazabicyclo[5.4.0]-7-undecene; and inorganic bases such as sodium hydroxide, potassium carbonate, and sodium carbonate, alone or in admixture of any. An appropriate amount of the catalyst used is 0.001 to 5.0 mol, and especially 0.001 to 0.1 mol per mol of the ester compound (5). The reaction temperature is preferably in the range of about 50 to 200° C. although it depends on other reaction conditions. It is desirable that the reaction be carried out while removing the alcohol ($R^5OH$) which is formed by the reaction. From the yield standpoint, the reaction is desirably continued to completion while monitoring the reaction by gas chromatography (GC) or silica gel thin layer chromatography (TLC), although the reaction time is usually about 0.5 to about 20 hours. From the reaction mixture, the end tertiary alcohol compound (1) is obtained by a conventional aqueous work-up step. If necessary, the end compound is purified by any conventional technique such as distillation or chromatography.

A polymer is prepared using the inventive tertiary alcohol compound as a monomer. The method generally involves the steps of mixing the monomer with a solvent, adding a catalyst or polymerization initiator, and effecting polymerization reaction while heating or cooling the system if necessary. This polymerization reaction can be effected in a conventional way. Suitable polymerization procedures include ring-opening metathesis polymerization, addition polymerization, and alternating copolymerization with maleic anhydride or maleimide. If desired, another norbornene or (meth)acrylate type monomer can be copolymerized.

A resist composition is formulated using as a base resin the polymer resulting from polymerization of the tertiary alcohol compound. Usually, the resist composition is formulated by adding an organic solvent and a photoacid generator to the polymer and if necessary, further adding a crosslinker, a basic compound, a dissolution inhibitor and other additives. Preparation of the resist composition can be effected in a conventional way.

The resist composition formulated using the polymer resulting from polymerization of the inventive tertiary alcohol compound lends itself to micropatterning with electron beams or deep-UV rays since it is sensitive to high-energy radiation and has excellent sensitivity, resolution, etching resistance and adhesion to substrates. Especially because of the minimized absorption at the exposure wavelength of an ArF or KrF excimer laser, a finely defined pattern having sidewalls perpendicular to the substrate can easily be formed. The resist composition is thus suitable as micropatterning material for VLSI fabrication.

EXAMPLE

Synthesis Examples and Reference Examples are given below for further illustrating the invention. It is not construed that the invention be limited to these examples.

Synthesis Examples are first described. Tertiary alcohol compounds within the scope of the invention were synthesized in accordance with the following formulation.

Synthesis Example 1

Synthesis 1 of 4-hydroxy-4-methylpentyl 5-norbornene-2-carboxylate (Monomer 1)

To a mixture of 118 g of 4-methyl-1,4-pentanediol, 111 g of triethylamine and 400 ml of toluene at 20° C., 157 g of 5-norbornene-2-carbonyl chloride was added over one hour. After 5 hours of stirring, 200 ml of water was added to the reaction solution to stop the reaction whereupon the mixture separated. The organic layer was washed with water and saturated sodium chloride water, dried over anhydrous sodium sulfate, and concentrated in vacuum. It was purified by vacuum distillation, collecting 214 g of 4-hydroxy-4-methylpentyl 5-norbornene-2-carboxylate (boiling point: 111–113° C./27 Pa, yield: 90%).

IR (thin film): ν=3502, 3434, 3060, 2970, 2875, 1732, 1469, 1448, 1379, 1336, 1270, 1190, 1188, 1066, 1031, 950, 906, 839, 814, 777, 712 cm$^{-1}$ $^1$H-NMR of major isomer (270 MHz in CDCl$_3$): δ=1.25 (6H, s), 1.37–1.54 (6H, m), 1.59–1.74 (2H, m), 1.84–1.93 (1H, m), 2.90–2.95 (2H, m), 3.12 (1H, s), 4.01 (2H, t), 5.91 (1H, m), 6.16 (1H, m)

Synthesis Example 2

Synthesis 2 of 4-hydroxy-4-methylpentyl 5-norbornene-2-carboxylate (Monomer 1)

A mixture of 118 g of 4-methyl-1,4-pentanediol, 173 g of methyl 5-norbornene-2-carboxylate, 1.4 g of sodium methoxide and 400 ml of toluene was heated under reflux for 5 hours while distilling off the methanol which formed during the reaction. The reaction solution was cooled, washed with saturated sodium bicarbonate water, dried over anhydrous sodium sulfate, and concentrated in vacuum. It was purified by vacuum distillation, collecting 221 g of 4-hydroxy-4-methylpentyl 5-norbornene-2-carboxylate (yield: 93%). The physical data of this product were in good coincidence with those of Synthesis Example 1.

Synthesis Example 3

Synthesis of 4-hydroxy-4-methylpentyl 2-(5-norbornen-2-yl)acetate (Monomer 2)

By following the procedure of Synthesis Example 2 except that methyl 2-(5-norbornen-2-yl)acetate was used instead of methyl 5-norbornene-2-carboxylate, there was obtained 4-hydroxy-4-methylpentyl 2-(5-norbornen-2-yl)acetate. Yield 93%.

Synthesis Example 4

Synthesis of 4-hydroxy-4-methylpentyl 8-tetracyclo-[4.4.0.1$^{2,5}$.1$^{7,10}$]dodecene-3-carboxylate (Monomer 3)

By following the procedure of Synthesis Example 2 except that methyl 8-tetracyclo[4.4.0.1$^{2,5}$.1$^{7,10}$]dodecene-3-carboxylate was used instead of methyl 5-norbornene-2-carboxylate, there was obtained 4-hydroxy-4-methylpentyl 8-tetracyclo[4.4.0.1$^{2,5}$0.1$^{7,10}$]dodecene-3-carboxylate. Yield 88%.

Synthesis Example 5

Synthesis of 4-ethyl-4-hydroxyhexyl 5-norbornene-2-carboxylate (Monomer 4)

By following the procedure of Synthesis Example 2 except that 4-ethyl-1,4-hexanediol was used instead of 4-methyl-1,4-pentanediol, there was obtained 4-ethyl-4-hydroxyhexyl 5-norbornene-2-carboxylate. Yield 91%.

IR (thin film): ν=3513, 3062, 2966, 2879, 1729, 1461, 1386, 1334, 1272, 1232, 1176, 1110, 1064, 1031, 950, 860, 838, 777, 712 cm$^{-1}$ $^1$H-NMR of major isomer (300 MHz in CDCl$_3$): δ=0.85 (6H, t), 1.27–1.52 (10H, m), 1.59–1.66 (2H, m), 1.88–1.94 (1H, m), 2.88–2.95 (2H, m), 3.19 (1H, s), 4.02 (2H, t), 5.92 (1H, m), 6.17 (1H, m)

Synthesis Example 6

Synthesis of 4-ethyl-4-hydroxyhexyl 8-tetracyclo-[4.4.0.1$^{2,5}$.1$^{7,10}$]dodecene-3-carboxylate (Monomer 5)

By following the procedure of Synthesis Example 2 except that 4-ethyl-1,4-hexanediol was used instead of 4-methyl-1,4-pentanediol and methyl 8-tetracyclo-[4.4.0.1$^{2,5}$.1$^{7,10}$]dodecene-3-carboxylate used instead of methyl 5-norbornene-2-carboxylate, there was obtained 4-ethyl-4-hydroxyhexyl 8-tetracyclo[4.4.0.1$^{2,5}$.1$^{7,10}$]dodecene-3-carboxylate. Yield 89%.

IR (thin film): ν=3513, 3050, 2962, 2879, 1729, 1458, 1389, 1358, 1315, 1286, 1250, 1219, 1180, 1109, 1072, 1039, 951, 925, 900, 850, 800, 773, 748, 721 cm$^{-1}$ $^1$H-NMR of major isomer (300 MHz in CDCl$_3$): δ=0.65–0.84 (1H, m), 0.85 (6H, t), 1.16 (1H, d), 1.26–1.78 (12H, m), 1.98–2.10 (5H, m), 2.38 (1H, m), 2.77–2.87 (2H, m), 3.19 (1H, s), 4.03 (2H, t), 5.94 (2H, m)

Synthesis Example 7

Synthesis of 4-ethyl-4-hydroxyhexyl 3-(5-norbornen-2-yl)propionate (Monomer 6)

By following the procedure of Synthesis Example 2 except that 4-ethyl-1,4-hexanediol was used instead of 4-methyl-1,4-pentanediol and methyl 3-(5-norbornen-2-yl) propionate used instead of methyl 5-norbornene-2-carboxylate, there was obtained 4-ethyl-4-hydroxyhexyl 3-(5-norbornen-2-yl)propionate. Yield 91%.

Synthesis Example 8

Synthesis of 5-hydroxy-5-methylhexyl 5-norbornene-2-carboxylate (Monomer 7)

By following the procedure of Synthesis Example 2 except that 5-methyl-1,5-hexanediol was used instead of 4-methyl-1,4-pentanediol, there was obtained 5-hydroxy-5-methylhexyl 5-norbornene-2-carboxylate (boiling point: 117–119° C./27 Pa, yield: 94%).

IR (thin film): ν=3502, 3434, 3060, 2969, 2871, 1729, 1467, 1377, 1334, 1272, 1232, 1176, 1110, 1068, 1035, 954, 908, 862, 839, 775, 711 cm$^{-1}$ $^1$H-NMR of major isomer (300 MHz in CDCl$_3$): δ=1.20 (6H, s), 1.31–1.52 (8H, m), 1.56–1.78 (2H, m), 1.86–1.92 (1H, m), 2.85–2.96 (2H, m), 3.18 (1H, m), 3.94–4.07 (2H, m), 5.91 (1H, m), 6.16 (1H, m)

Synthesis Example 9

Synthesis of 5-hydroxy-5-methylhexyl 4-(5-norbornen-2-yl)butyrate (Monomer 8)

By following the procedure of Synthesis Example 2 except that 5-methyl-1,5-hexanediol was used instead of 4-methyl-1,4-pentanediol and methyl 4-(5-norbornen-2-yl) butyrate used instead of methyl 5-norbornene-2-carboxylate, there was obtained 5-hydroxy-5-methylhexyl 4-(5-norbornen-2-yl)butyrate. Yield 92%.

Synthesis Example 10

Synthesis of 5-hydroxy-5-methylheptyl 5-norbornene-2-carboxylate (Monomer 9)

By following the procedure of Synthesis Example 2 except that 5-methyl-1,5-heptanediol was used instead of 4-methyl-1,4-pentanediol, there was obtained 5-hydroxy-5-methylheptyl 5-norbornene-2-carboxylate. Yield 92%.

Synthesis Example 11

Synthesis of 5-hydroxy-5-methylheptyl 3-(8-tetracyclo-[4.4.0.1$^{2,5}$.1$^{7,10}$]dodecen-3-yl)propionate (Monomer 10)

By following the procedure of Synthesis Example 2 except that 5-methyl-1,5-heptanediol was used instead of 4-methyl-1,4-pentanediol and methyl 3-(8-tetracyclo-[4.4.0.1$^{2,5}$.1$^{7,10}$]dodecen-3-yl)propionate used instead of methyl 5-norbornene-2-carboxylate, there was obtained 5-hydroxy-5-methylheptyl 3-(8-tetracyclo[4.4.0.1$^{2,5}$.1$^{7,10}$]-dodecen-3-yl)propionate. Yield 87%.

Synthesis Example 12

Synthesis of 3-(1-hydroxycyclopentyl)propyl 5-norbornene-2-carboxylate (Monomer 11)

By following the procedure of Synthesis Example 2 except that 1-(3-hydroxypropyl)cyclopentanol was used instead of 4-methyl-1,4-pentanediol, there was obtained 3-(1-hydroxycyclopentyl)propyl 5-norbornene-2-carboxylate. Yield 93%.

Synthesis Example 13

Synthesis of 3-(1-hydroxycyclopentyl)propyl 8-tetracyclo-[4.4.0.1$^{2,5}$.1$^{7,10}$]dodecene-3-carboxylate (Monomer 12)

By following the procedure of Synthesis Example 2 except that 1-(3-hydroxypropyl)cyclopentanol was used instead of 4-methyl-1,4-pentanediol and methyl 8-tetracyclo-[4.4.0.1$^{2,5}$.1$^{7,10}$]dodecene-3-carboxylate used instead of methyl 5-norbornene-2-carboxylate, there was obtained 3-(1-hydroxycyclopentyl)propyl 8-tetracyclo [4.4.0.1$^{2,5}$.1$^{7,10}$]-dodecene-3-carboxylate. Yield 88%.

Synthesis Example 14

Synthesis of 4-hydroxy-4-methylhexyl 5-norbornene-2-carboxylate (Monomer 13)

By following the procedure of Synthesis Example 2 except that 4-methyl-1,4-hexanediol was used instead of 4-methyl-1,4-pentanediol, there was obtained 4-hydroxy-4-methylhexyl 5-norbornene-2-carboxylate. Yield 94%.

Synthesis Example 15

Synthesis of 2-hydroxy-2-methylpropyl 5-norbornene-2-carboxylate (Monomer 14)

By following the procedure of Synthesis Example 2 except that 2-methyl-1,2-propanediol was used instead of 4-methyl-1,4-pentanediol, there was obtained 2-hydroxy-2-methylpropyl 5-norbornene-2-carboxylate. Yield 94%.

Synthesis Example 16

Synthesis of 5,5-dicyclohexyl-5-hydroxypentyl 5-norbornene-2-carboxylate (Monomer 15)

By following the procedure of Synthesis Example 2 except that 5,5-dicyclohexyl-1,5-pentanediol was used instead of 4-methyl-1,4-pentanediol, there was obtained 5,5-dicyclohexyl-5-hydroxypentyl 5-norbornene-2-carboxylate. Yield 90%.

The structural formulas of Monomers 1 to 15 are shown below.
(Monomer 1)
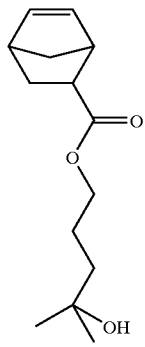
(Monomer 2)
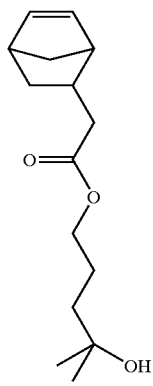
(Monomer 3)
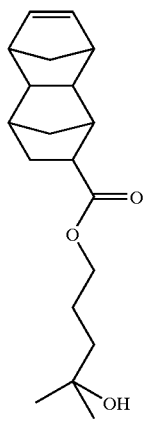
(Monomer 4)
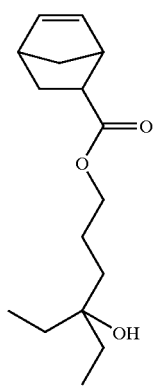
(Monomer 5)
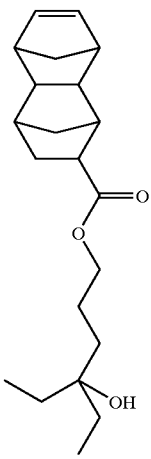
(Monomer 6)
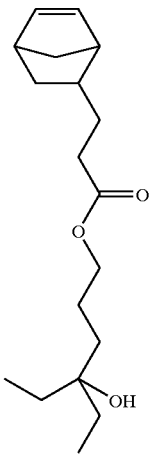
(Monomer 7)
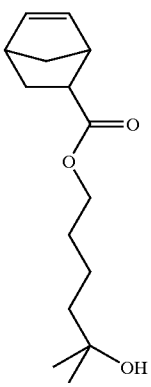

(Monomer 8)
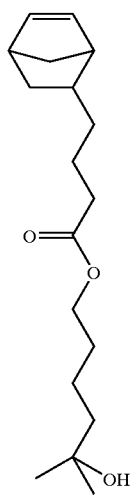
(Monomer 11)
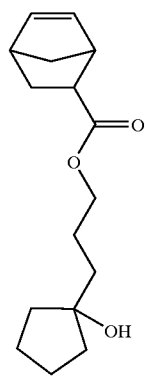
(Monomer 9)
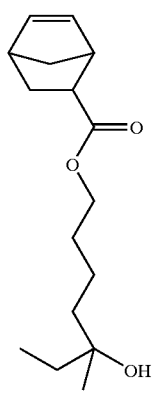
(Monomer 12)
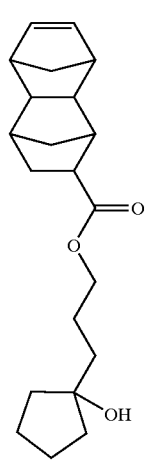
(Monomer 10)
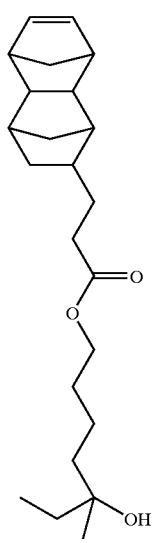
(Monomer 13)
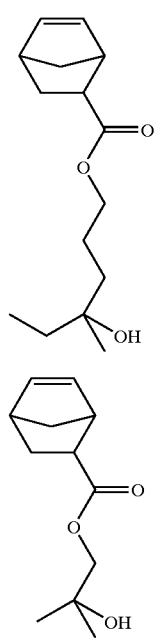
(Monomer 14)

(Monomer 15)

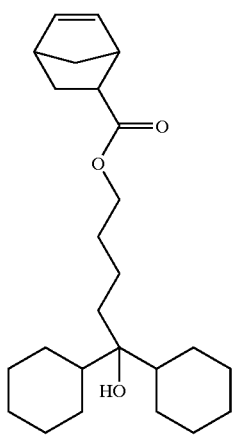

Reference Example

Polymers were synthesized using the tertiary alcohol compounds obtained in the above Synthesis Examples. Resist compositions were formulated using the polymers as the base resin and examined for substrate adhesion.

Polymerization reaction was effected on tert-butyl 5-norbornene-2-carboxylate, Monomer 1, and maleic anhydride using the initiator V60 (by Wako Junyaku K. K.), yielding an alternating copolymer of tert-butyl 5-norbornene-2-carboxylate/4-hydroxy-4-methylpentyl 5-norbornene-2-carboxylate/maleic anhydride in a ratio of 4/1/5.

A resist composition was prepared by dissolving 80 parts by weight of the base resin, 1.0 part by weight of triphenylsulfonium trifluoromethanesulfonate as the photoacid generator, and 0.08 part by weight of tri-n-butylamine in 480 parts by weight of propylene glycol monomethyl ether acetate as the solvent. The resist solution was spin coated onto hexamethyldisilazane-spray coated silicon wafers at 90° C. for 40 seconds, then heat treated at 110° C. for 90 seconds to give a resist film having a thickness of 500 nm. The resist film was exposed to an KrF excimer laser beam, then heat treated at 110° C. for 90 seconds, and dip developed with a solution of 2.38% tetramethylammonium hydroxide in water for 60 seconds, thereby giving a 1:1 line-and-space pattern. The wafer as developed was observed under top down SEM, finding that the lines down to 0.25 μm were left unstrapped.

Comparative Reference Example

For comparison purposes, a resist composition was prepared according to the same formulation as above using an alternating copolymer of tert-butyl 5-norbornene-2-carboxylate/maleic anhydride in a ratio of 1/1. This was similarly applied, exposed and processed. In the substrate adhesion test, those lines of 0.50 μm and less were not left.

It was confirmed that polymers resulting from the inventive tertiary alcohol compounds have very high substrate adhesion as compared with prior art polymers.

Japanese Patent Application No. 2000-378693 is incorporated herein by reference.

Although some preferred embodiments have been described, many modifications and variations may be made thereto in light of the above teachings. It is therefore to be understood that the invention may be practiced otherwise than as specifically described without departing from the scope of the appended claims.

What is claimed is:

1. A tertiary alcohol compound of formula (1):

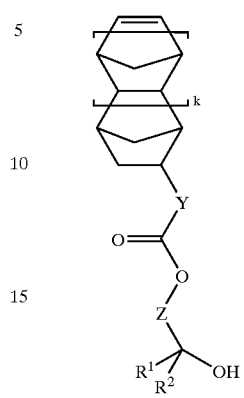

(1)

wherein $R^1$ and $R^2$ are independently a straight, branched or cyclic alkyl group of 1 to 10 carbon atoms in which some or all of the hydrogen atoms on constituent carbon atoms are optionally substituted with halogen atoms, or $R^1$ and $R^2$, taken together, may form an aliphatic hydrocarbon ring, Y and Z are independently a single bond or a straight, branched or cyclic divalent organic group made up of 1 to 10 carbon atoms, and k is 0 or 1, with the proviso that the compound of formula (1) is not

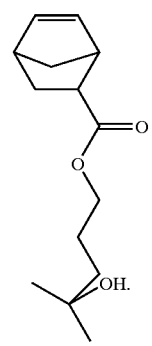

2. A tertiary alcohol compound of formula (2):

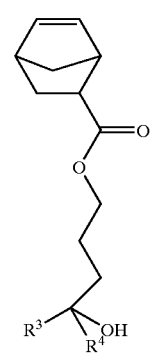

(2)

wherein $R^3$ and $R^4$ are independently a straight, branched or cyclic alkyl group of 1 to 6 carbon atoms, with the proviso that $R^3$ and $R^4$ are not both methyl.

3. A tertiary alcohol compound of formula (1):

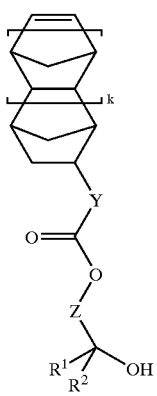

(1)

wherein $R^1$ and $R^2$ are independently a straight, branched or cyclic alkyl group of 1 to 10 carbon atoms in which some or all of the hydrogen atoms on constituent carbon atoms are optionally substituted with halogen atoms, or $R^1$ and $R^2$, taken together, may form an aliphatic hydrocarbon ring, Y is a straight, branched or cyclic divalent organic group made up of 1 to 10 carbon atoms, Z is a single bond or a straight, branched or cyclic divalent organic group of 1 to 10 carbon atoms, and k is 0 or 1.

4. A tertiary alcohol compound of claim 1, wherein $R^1$ and $R^2$ have 1 to 6 carbon atoms.

5. A tertiary alcohol compound of claim 3, wherein $R^1$ and $R^2$ have 1 to 6 carbon atoms.

6. A tertiary alcohol compound of claim 1, wherein k is 1.

7. A tertiary alcohol compound of claim 3, wherein k is 1.

8. A tertiary alcohol compound of claim 1, which is selected from the group consisting of

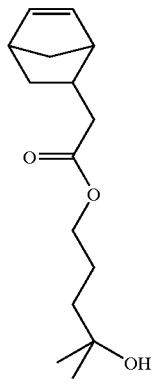

(Monomer 2)

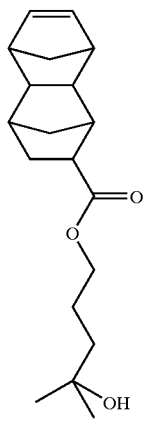

(Monomer 3)

-continued

(Monomer 4)

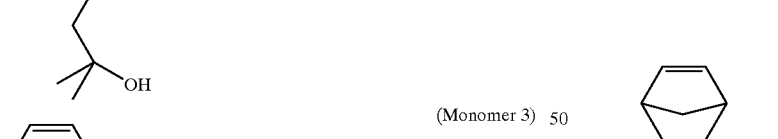

(Monomer 5)

(Monomer 6)

(Monomer 7)
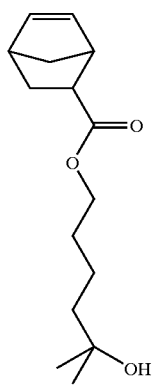
(Monomer 10)
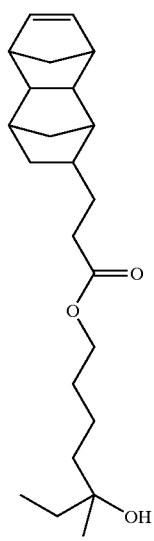
(Monomer 8)
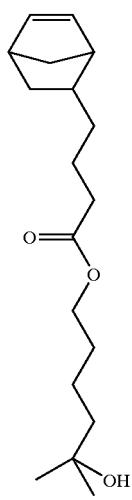
(Monomer 11)
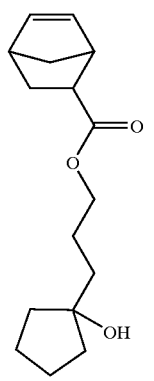
(Monomer 9)
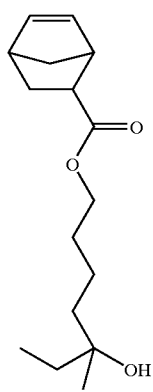
(Monomer 12)
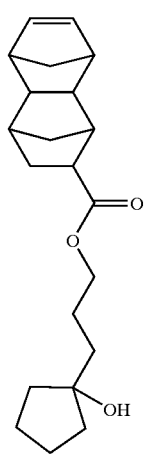

-continued
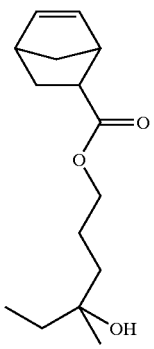
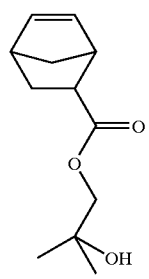 and
(Monomer 13)
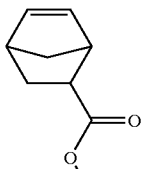
(Monomer 14)
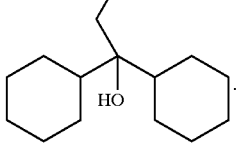
(Monomer 15)
* * * * *